(12) United States Patent
Nakamura et al.

(10) Patent No.: US 6,926,819 B2
(45) Date of Patent: Aug. 9, 2005

(54) METHOD FOR GENERATING STERILIZING WASH WATER AND A PORTABLE APPARATUS THEREOF

(75) Inventors: Shinichi Nakamura, Osaka (JP); Kunihiko Fukuzuka, Osaka (JP); Masaki Miyashita, Osaka (JP)

(73) Assignee: Omega Co. Ltd., Osaka (JP)

( * ) Notice: Subject to any disclaimer, the term of this patent is extended or adjusted under 35 U.S.C. 154(b) by 264 days.

(21) Appl. No.: 10/153,803

(22) Filed: May 24, 2002

(65) Prior Publication Data

US 2003/0062267 A1 Apr. 3, 2003

(30) Foreign Application Priority Data

May 25, 2001 (JP) ........................................ 2001-157680

(51) Int. Cl.[7] ............................................... C02F 1/461
(52) U.S. Cl. ........................ 205/701; 205/742; 205/556; 204/275.1; 204/272; 204/274
(58) Field of Search ................................ 205/701, 742, 205/556; 204/275.1, 272, 274; 29/592.1

(56) References Cited

U.S. PATENT DOCUMENTS 5,858,201 A * 1/1999 Otsuka et al. .............. 205/701

6,113,853 A * 9/2000 Nakamura et al. ............ 422/23
6,699,381 B2 * 3/2004 Nakamura et al. .......... 205/701

FOREIGN PATENT DOCUMENTS

| JP | 10-328665 | 12/1998 |
|---|---|---|
| JP | 11-347557 | 12/1999 |
| JP | 2000-107252 | 4/2000 |
| JP | 2000-153278 | 6/2000 |
| JP | 2001-276826 | 10/2001 |
| JP | 2002-017829 | 1/2002 |
| JP | 2002-052074 | 2/2002 |

* cited by examiner

Primary Examiner—Arun S. Phasge
(74) Attorney, Agent, or Firm—Rader, Fishman & Grauer PLLC

(57) ABSTRACT

In a method and an apparatus for generating a portable sterilizing water that can be easily used at, for example, hospitals, cafeterias of nursing facilities, restaurants, hair salons or homes, an electrolyzer is structured such that a tubular-shaped ferrite anode and a cathode are arranged alternately in a concentric manner with an inter-electrode distance, and integrated with a pressurizable solution container containing halogen ions and a power control apparatus so that it can be carried and operated by one hand.

10 Claims, 4 Drawing Sheets

METHOD FOR GENERATING STERILIZING WASH WATER AND A PORTABLE APPARATUS THEREOF

BACKGROUND OF THE INVENTION

The present invention relates to a method and apparatus for sterilizing wash water. The apparatus can be simply transported to any location and can be operated with one hand as needed, even in locations where there is no power or water supply facilities, or in a limited space.

Currently, an agent such as ethyl alcohol, benzalkonium chloride, chlorhexidine hydrochloride or a chlorhexidine gluconate solution is used for disinfection/sterilization, at clinical and nursing sites, and kitchens, for kitchen tools. However, even though these agents are used, there are a variety of harmful effects such as rough skin and water pollution or at hospitals, or infections are not sufficiently prevented.

In order to prevent these harmful effects, recently, technology employing electrolyzed acidic water has been watched with keen interest. Namely, it has been known that by using a diaphragm, when electrolysis is carried out by adding an electrolyte such as a small amount of salt, a highly active nascent oxygen and chlorine are generated whereby acidic water from the anode chamber is created, while electrolyzed restoration water (alkaline ionic water) is generated from the cathode chamber. At this time, the acidic water obtained from the anode side has a pH of 2.7 or less, an oxidation-reduction potential of +1,100 mV or greater, and available chlorine of 30 to 40 ppm. It sterilizes a variety of bacteria when used even for a short period of time. However, it is strongly acidic with a pH of 2.7 or less, therefore, it has problems such as the causing of rough skin and the corrosion of tools.

In Japanese Laid-Open Patent Publication Nos. H06-292892, H 06-312011, H 11-226092, H 11-347557 and, H 12-070171 it is disclosed how to create sterlying water that has highly sterilizing effect and is slightly acidic or neutral. The sterlying water is made by electrolyzing a solution containing a bromine ion and other halogen ions, such as chlorine ions, and which is obtained by using an electrolyzer without a diaphragm.

The electrolyzed water obtained, in these prior arts, has a pH of 6 to 8 and yet has a superior sterilizing effect. The electrolyzed water with bromine ions and halogen ions adjusted to a certain ratio has a superior sterilizing effect even with a pH of 6 or greater. It demonstrates superior sterilizing power even though it is used for a short period of time. In addition, it has a superior sterilizing effect without causing rough skin or the corrosion of tools.

However, the sterilizing wash water obtained in the prior art, has a serious problem that installation locations for setting up the apparatus for manufacturing the sterilizing water are limited. It could not be easily moved at any time to another location, so that it is not convenient.

In Japanese Laid-Open Patent No. H 14-52074 entitled "A sterilizing wash spray product and its manufacturing method," this problem has been solved by filling electrolyzed water with a sterilizing effect into a spray container that blocks light and air, and which was under a pressurized inert gas.

However, even with this method, there is a problem that, when a long period of time has passed during the distribution stages, it is impossible to avoid a gradual decrease in the effectiveness.

In order to drastically reduce the problem, the development of a compact and light electrolyzer is necessary. Japanese Laid-Open Patent No. H11-235592 (Kobayashi et al.) discloses an electrolyzer, however, it is not compact and light enough to be operated with one hand.

The present inventors have been making an effort to develop a portable and yet highly electrolytically effective electrolyzer with a nickel-ferrite anode. Related to this ferrite electrode, the present inventors have filed the following patent applications.

(1) Japanese Laid-Open Patent No. H11-188364 "Electrolyzer"
(2) Japanese Laid-Open Patent No. H11-309458 "Electrolyzer"

In these inventions, a long-term durability performance is 3 to 5 times greater than that of the existing hand wash sterilizing water apparatus with a platinum-plated titanium electrode, under the same conditions.

(3) In Japanese Laid-Open Patent No. H13-347270 entitled "Electrolyzer," an electrolyzer with an additionally high electrolyzing efficiency is disclosed in which it is possible to minimize the electrolyzer. Nonetheless, it is impossible to provide a compact apparatus, which is easy to use and be operable with one hand, such as a hand spray.

Currently, problems of contagion are not limited to hospitals and nursing homes, but also schools, cafeterias, restaurants, hair salons. Thus, an easy to use sterilizing washing means has been strongly desired.

It is an objective of the present invention to provide a compact, light, easy to use, and inexpensive sterilizing washing method and means.

In order to solve the above-mentioned issue, the present invention provides a compact electrolyzer that can be held in one hand and operable while walking around. The present invention, for example, has the following basic structures.

(a) A 30 to 50 W switching power source is used as a direct current power device, and a rechargeable battery is contained in a power control device portion (2) as the power supply. This is integrated with an electrolyzer (1) and a pressurizable container (18) for a solution that is comprised of halogen ions, allowing an operation while being lightly held by one hand.

The amount the container contains of the electrolyte solution is as much as 100 to 500 ml. Therefore, a mixture of bromine ions and chlorine ions is used for the electrolyte so that a single spraying amount of 1 to 5 ml provides a sufficient sterilizing/washing effect.

(b) It is required for the electrolyzer (1) to be as compact as possible and to have a high electrolytic efficiency even for solutions with low electric conductivity, in order for the electrolyzer (1) to be able to be handled freely by one hand, and to be used on bodies to prevent pressure sores for patients and the aged on beds of hospitals, or on heads at barbers or hair salons. Therefore, the present invention is arranged and structured such that an anode (3) that is comprised of a conductive metal pipe or rod in which a thermal spraying film of ferrite is deposited on the metal surface, and a cathode (4) comprising a conductive metal pipe are alternated with an inter-electrode distance of cathode (4) comprising a metal pipe is alternated with its inter-electrode distance of 1.1 to 9 mm in a concentric manner. Electrolysis is carried out by flowing the solution comprised of the halogen ions in the inter-electrode space.

(c) When a ferrite pipe or a rod having a hole in the direction of the center axis, that has a high electrolysis efficiency and low electric conductivity is used, and when centered anode (3) is a ferrite pipe or rod, it is structured such that a conductive low melting point metal junction (6) or mercury is filled in the long hole, or a hole in the ferrite pipe, and then a rod shaped terminal body (5) that corresponds to the length of the electrode is inserted therein, to create a terminal. On its outside, a conductive anti-corrosive metal tube as a cathode (4) is concentrically placed with an appropriate inter-electrode distance.

Since the low melting point metal junction (6) has a low melting point and is soft, when the terminal body (5) is inserted, the low melting point metal is forced into the gap between the terminal body (5) and the nickel-ferrite pipe (3) without any spaces, serving as a electrical binder for the terminal body (5) and the nickel-ferrite pipe (3). At this point, it is further advantageous to use the low melting point metal in a fluid state by heating it to around its melting point, or to use mercury, which is liquid at room temperatures. Mercury creates a mercury amalgam with copper, tin, and lead, and therefore, in the case that the terminal body (5) is made of these metals, the surface of the terminal body (5) becomes a soft amalgam and has even better adhesion, even when the gap between the terminal body (5) and with the nickel-ferrite electrode is narrower.

(d) It has a compact structure without having a pump or pipes so that it can be used as a portable generator of sterilizing wash water. Therefore, the volume of the container (18) of electrolyte solution required for electrolysis is 100 to 500 ml. The container (18) is easily attachable/ detachable to the fee hole of the electrolyzer body. The container (10) is filled with a solution containing halogen ions, and pressure is applied by operating an air pump, so that when the valve of the feed hole (19) of the solution containing halogen ions opens, an electrolyte solution is fed to the electrolyzer.

If a plurality of containers (18) of the solution containing halogen ions can be prepared so that the container (18) can be immediately replaced and used when the solution runs out. For different purposes, a solution with a different combination of halogen ions and concentration can be prepared.

(e) A pressurized air or inert gas inlet (26) is provided in the container (18) for the solution containing halogen ions. When the internal pressure is decreased or the solution is refilled after running out, the air pump or inert gas supplying means is mounted on this inlet (26) so that it can be used for applying air pressure or a pressure from pressurized inert gas.

(f) Bromine ions and chlorine ions can be used individually, or a mixture of bromine ions and chlorine ions can be used. However, in order for the apparatus to be portable and compact, it is desirable to use a mixture of bromine ions and chlorine ions so that it has as high a sterilizing and sanitizing effect as possible with a small amount of electrolyte solution used. In addition, to further increase its effect, it is desirable for the mol ratio of bromine ions and chlorine ions to be 50:50 to 70:30.

When the flow of the electrolytic current and solution containing halogen ions is designated, the higher the concentration of the halogen ion, the higher the free residual chlorine concentration of the generated electrolyzed water. Therefore, depending on the required free residual chlorine concentration, it can be easily deal with such a case by replacing the container (18) with a prepared container (18) with a solution containing halogen ions with a different concentration.

(g) A battery or rechargeable battery is used for the power source so that it can be portable and operable with one hand. There is a small rectification circuit for the switching power that is commercially available so that it can be directly connected with a cord to an alternating current.

A power control device (2) in which this direct current power board and a control board which controls the electrolysis time, and a battery or rechargeable battery container are incorporated inside the electrolyzer fastener (23) that supports the electrolyzer (1). In addition, this electrolyzer fastener (23) supports the container (18) of the pressurizable solution as well. A portion of it serves as a handle (24) so that the entire apparatus can be operated with one hand.

(h) Electrolyzed sterilizing wash water can be sprayed on a target with the pressure of a pressurizable container (18) of solution by attaching a spray nozzle to the sterilizing wash water exit hole (17). In addition, without an attachment, electrolyzed sterilizing wash water can be removed to an appropriate container.

To remove any deposition such as hydroxide metals deposited on cathodes, an inorganic acid such as chlorine or an organic acid such as acetic acid is filled in a pressurizable container (18) for a solution in advance, and it is stored in a pressurized state by force filling an inert gas or atmosphere, and then this container is attached to a feed hole (19), and the valve of the feed connection (19) is opened and this acidic solution is introduced into the electrolyzer (1). Then deposits such as hydroxide metals are dissolved with an acidic solution with a pH of 1 to 3 and can be removed.

PREFERRED EMBODIMENTS OF THE INVENTION

The mode for carrying out the invention is described by referring to figures based on the embodiments.

Figure 1:
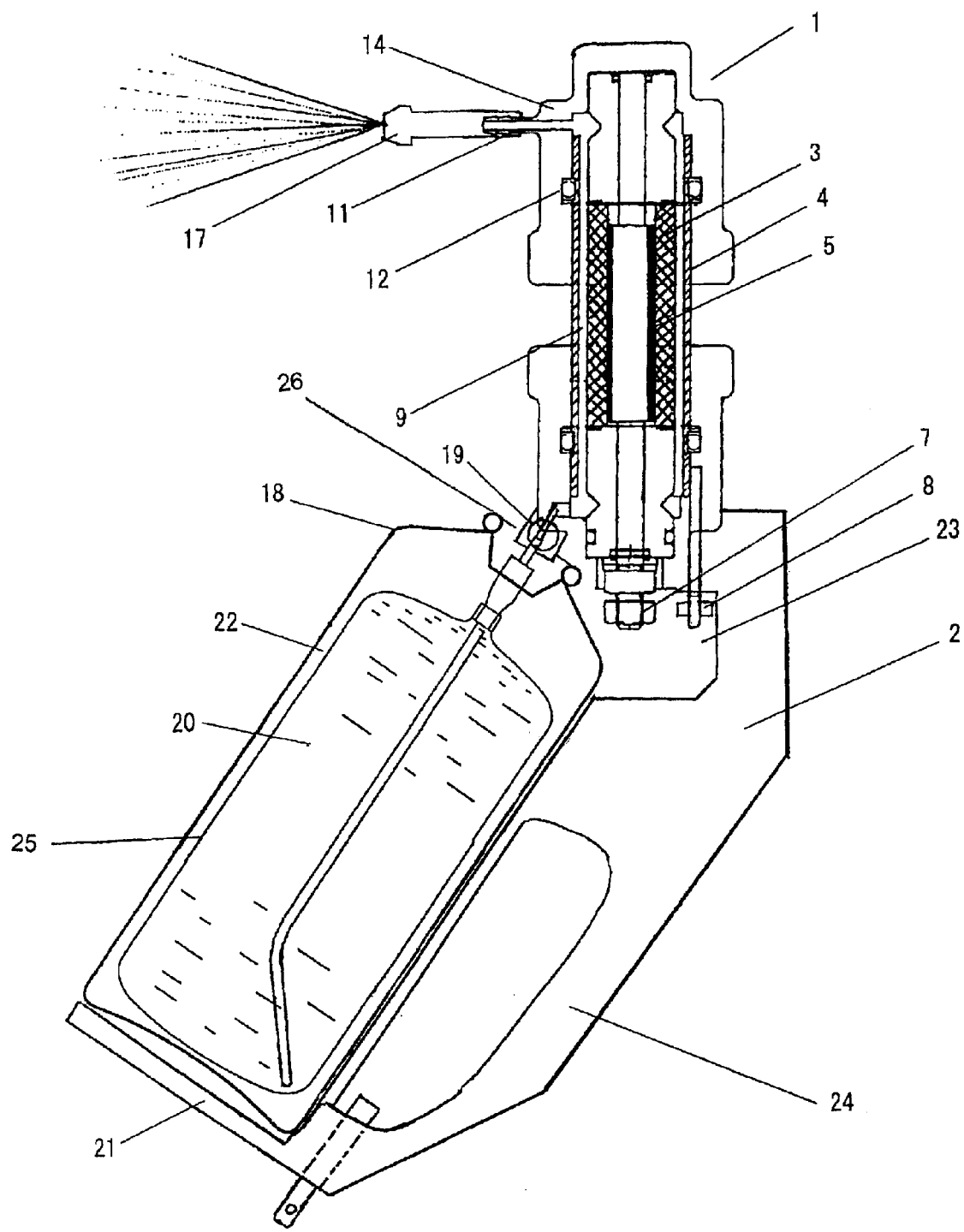
FIG. 1 is a portable production device for sterilizing wash water.

In FIG. 1, an electrolyzer (1) is mounted on the top of a power control apparatus (2) by a electrolyzer fastener (23), and a pressurizable solution container (18) is connected by its tip to a feed connection (19) of the electrolyzer (1), while the container (18) is held on a container support (21) that is located at the bottom of the electrolyzer fastener (23).

A direct current board, control board, battery or rechargeable battery, etc., for the electrolyzer (1) are contained inside the power control apparatus (2). In addition, a rectification circuit board for the switch power source is included in order for the electrolyzer to be connected with a cord to an alternating power supply.

A portion of the electrolyzer fastener (23) has a function as a handle (24) in order to allow an operator to handle it as a hand spray.

(Embodiment 1)

As shown in FIG. 1, in Embodiment 1, a double container (a bag-in-a-can type container), which has been normally used as a pressurizable solution spray container (18) is used.

A solution (20) containing halogen ions is filled in while the container (18) is detached from a feed connection (19) having a valve, and the valve is opened.

Then a pressurized atmosphere or pressurized inert gas (22) is filled from the gas inlet (26) to a space between the container (18) and outside the bag (25). The desirable pressure is 0.6 to 1.0 MPa, and in this embodiment an air pressure of 0.9 MPa is set.

If a container (18) with an anti-corrosive interior is used, the solution (20) containing halogen ions can be directly filled in without using a bag, and the pressurized air or pressurized inert gas can be filled in to the container (18) from the gas inlet (26).

As the solution containing halogen ions, a chloride or bromide of potassium or sodium is used individually or by mixing. Selection is made by changing the combination, ratio or concentration thereof, depending on purposes.

By using different combinations and ratios, and concentrations of the chloride and bromide, the solution can be used for a variety of objects. In addition, preparing the solution containers (18) containing different halogen ion combinations, ratios and concentrations in a 200 to 500 ml container in advance allows to sanitize or sterilize different objects with the same compact electrolyzed water generator.

Figure 2:
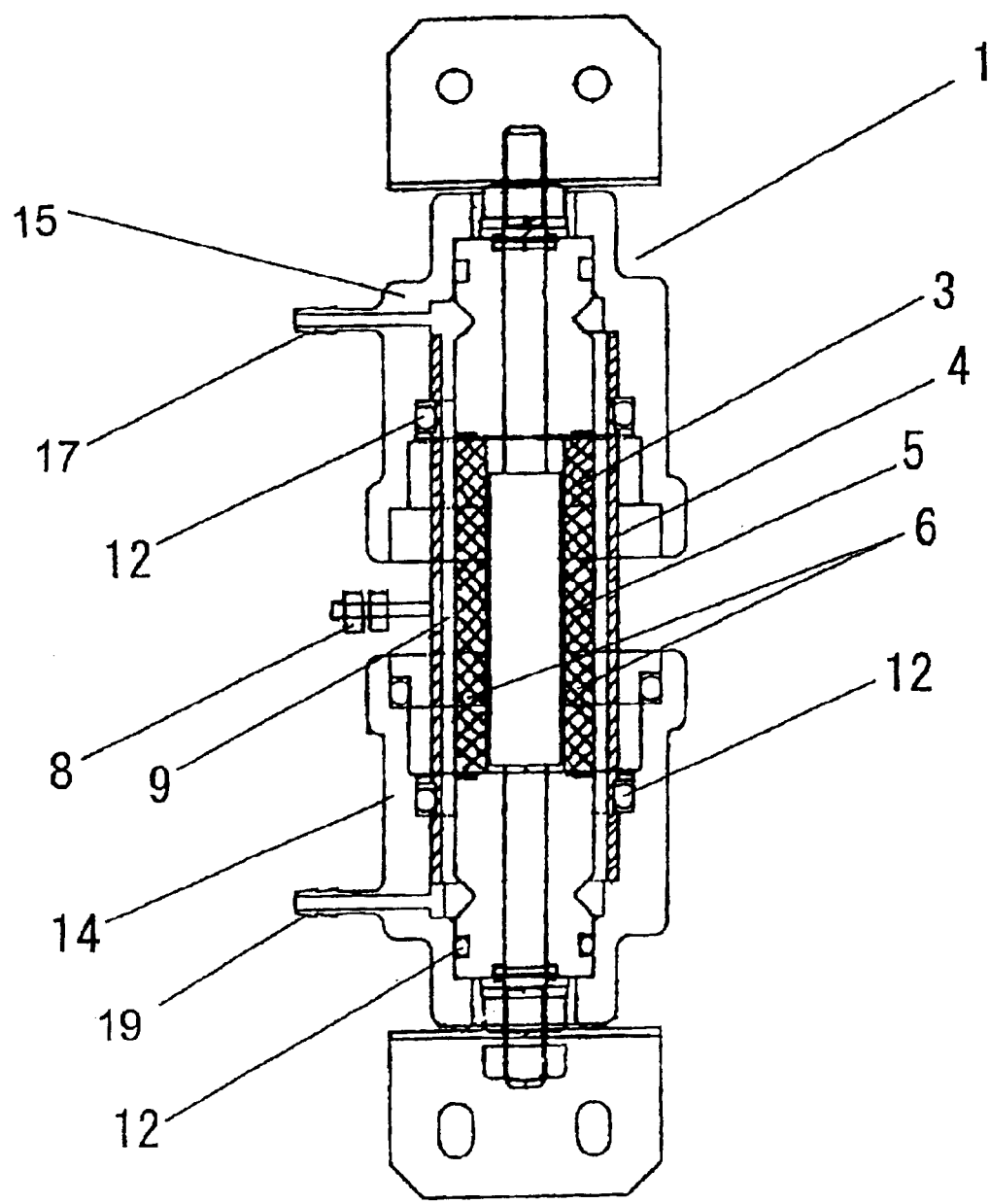
FIG. 2 is a cross-sectional view showing an electrolyzer comprising a barrel-shaped anode and a cathode having a terminal body and a low melting point metal junction inserted inside the cathode.

FIG. 2 shows an electrolyzer (1) used in the present embodiment. A 95 mm length tubular-shaped nickel-ferrite anode (3) and a tubular-shaped titanium cathode (4) on the outside are concentrically arranged. The inter-electrode distance of 2.5 mm is set. (An inter-electrode distance 1.1 to 9 mm is desirable.) The terminal of the titanium (4) cathode on the outside is a commonly available product, however, the nickel-ferrite anode (3) had a soft conductive low-melting point metal or mercury (6) which is filled into the pipe of the anode in advance (3), and then a rod-shaped terminal body (5) that correspondeds to the length of the electrode is inserted to create a terminal, allowing the contact area of the ferrite electrode and the terminal to be sufficiently large. In addition, it has the durable structure of a tubular shape having a good air-tightness from sealing, so that even mercury can be used safely. The rod may be coated with a ferrite by spraying melted ferrite. Accordingly, a sufficient wide contact area for the ferrite electrode, which is highly anti-corrosive and inexpensive in comparison to a platinum-plated one, with the terminal is obtained. The gap between the terminals and the electrode can be bound with a soft conductive low-melting point metal or mercury providing a superior electric conductivity, and consequently, a sanitizing/sterilizing water with a high free residual chlorine concentration can be generated with an extremely small electrode area.

In the present embodiment, in the vertically arranged electrode fastener-bottom (14), a terminal body (5), a nickel-ferrite anode (3), and a titanium cathode (4) on the outside are concentrically arranged. The bottom of each is sufficiently sealed with a gasket and an O-ring (12), and then mercury (6) was slowly filled in between the anode (3) and the terminal body (5). Although the mercury (6) that cannot fill the gap remains on the top of the terminal body (5), and then an electrode fastener-top (15) is covered from the top and sufficiently sealed with the gasket and o-ring (12).

The electrolyzer (1) is mounted and fixed on the top of a power control apparatus (2), and then the top portion of the pressurizable solution container (18) for a solution and the feed connection (19) are connected, and then it was positioned and fixed on top of the container supporter (21) at the bottom of the power control apparatus (2). The power control apparatus is started and the on/off operation is carried out by an operation button.

Further, the pressurizable solution container (18) is detachable from the feed connection (19) of the electrolyzer (1). The solution containing halogen is filled into the container in advance, and stored in a pressurized state by filling an inert gas or air. When the pressurizable solution container (18) become empty, the electrolyzer can be used after replacing the container. Thus, by using a detachable and pressurizable solution container (18), it can be easily replaced with a prepared spare container. Therefore, a portable hand spray is able to be created.

Further, an air pump or inert gas feeding means can be attached to the inlet of the pressurizable solution container. After filling the solution containing halogen ions, the container can be reused by applying air pressure or pressurized inert gas.

As long as an air pump or inert gas feeding means can be attached, the solution containing halogen ions can be filled at the site, and can be used immediately by pressurizing through force filling an inert gas or atmosphere.

When the operation button was turned "on", the valve of the feed connection (19) is opened and the solution containing halogen ions is fed from the pressurizable solution container (18) to the electrolyzer (1), and electrolysis is started. The electrolysis is controlled by the control board so that it is carried out while the valve is open and the solution is fed. The electrolyzed solution is moved up through an inner-electrode reactive portion (9) and is discharged from a spray nozzle (17) through a sterilizing wash water exit hole (11). In addition, other configurations for electrolysis such as a different electrolytic current or time can be set in a similar manner.

Further, the pressurizable solution container (18), the electrolyzer (1) with the ferrite anode (3), the power control apparatus combined with a sterilizing wash water exit hole (11), the battery or a rechargeable battery container or a cord connection with a 100V power (120V power), and a control board that configures and controls the direct power board and the electrolysis time, are integrated and structured so that they can be carried and operated by one hand, allowing the manufacturing of a portable compact electrolyzed water generating device.

Figure 3:
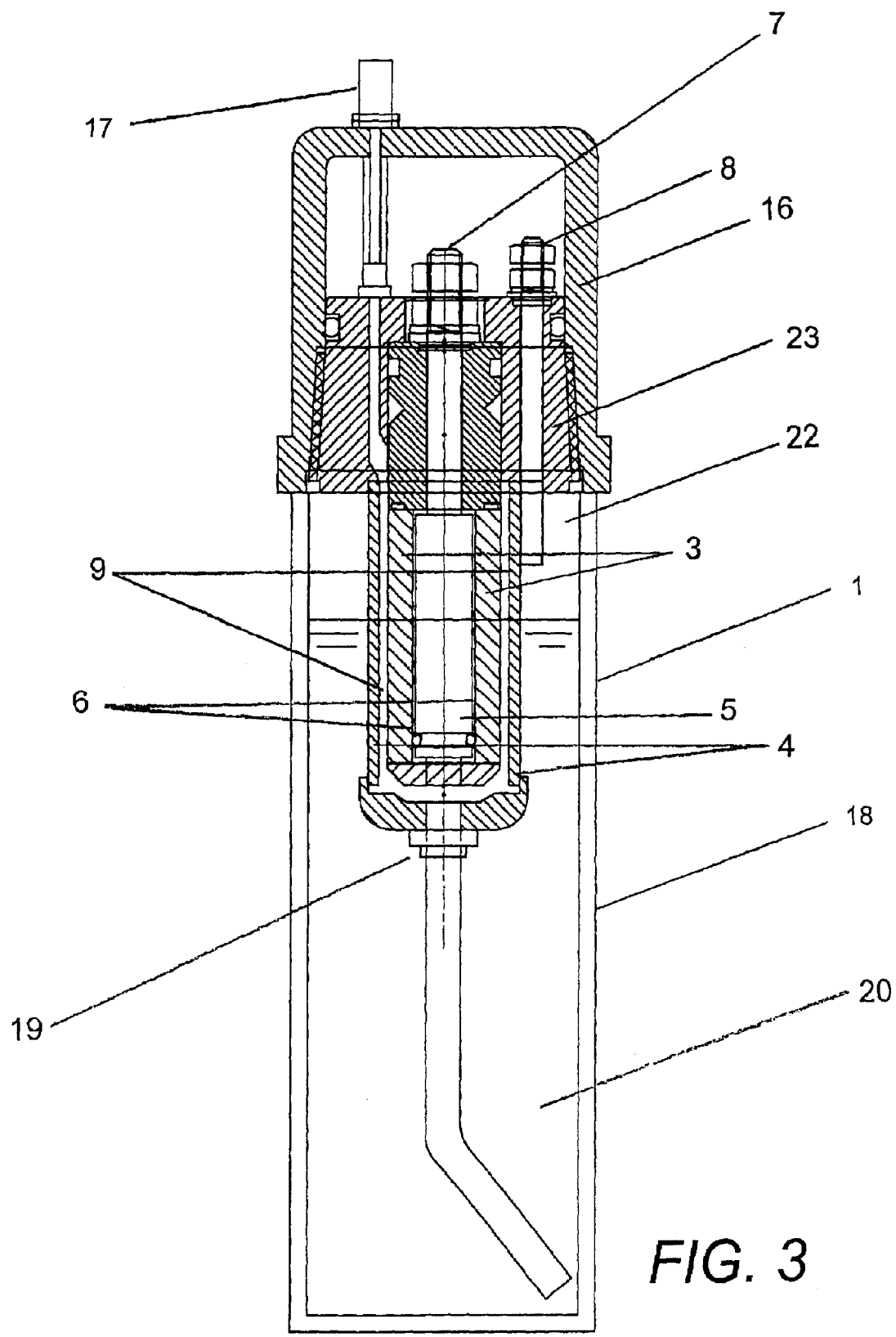
FIG. 3 is a cross-sectional view of an electrolytic spray container in which an electrolyzer (1) is dipped in a solution container (18) containing halogen ions, and a push-button-type spray nozzle (17) is attached on top. The electrolyzer (1) is connected to a power control apparatus (2) (not shown).

FIG. 3 is a cross-sectional view of an electrolytic spray, in which an electrolyzer (1) is dipped in a solution container (18) containing halogen ions. A push-button-type nozzle (17) is attached on the top.

As an embodiment of a "portable generation device for sterilizing wash water" of the present invention, a prototype of a sterilizing wash spray was created and a test was carried out.

As the solution containing halogen ions that was filled into the pressurizable solution container (18), the following (1) to (5) were used.

In the present embodiment, saline and sodium bromide were used with a weight ratio of 9:1 as the halogen ions. In Japanese Laid-Open Patent No. H11-226092 of the present inventors, the most desirable mol ratio is approximately 6:4. However, in this example, this ratio was selected based on the effect and the cost.

The following (1) to (5) were used, after changing the electric conductivity with the above-mentioned ratio, as the solution containing halogen ions filled into the pressurizable solution container (18).

(1) 507 $\mu$S/cm solution
(2) 1000 $\mu$S/cm solution
(3) 2060 $\mu$S/cm solution
(4) 3000 $\mu$S/cm solution
(5) 4000 $\mu$S/cm solution The electrode surface of the nickel-ferrite anode (3) was 1 dm2, and the amount of solution discharged from the sterilizing wash water exit hole (11) was 60 ml/min.

The results are shown in Table 1.

From these results, it was found that sanitizing/sterilizing water with the required free residual chlorine concentration can be generated as long as the electrolyte concentration is adjusted and a solution with a different electric conductivity is prepared.

TABLE 1

| | Current | | | | | | | |
|---|---|---|---|---|---|---|---|---|
| | 2A | | 3A | | 4A | | 5A | |
| | Electric Conductivity | | | | | | | |
| µS/cm | Voltage V | Free Residual Chlorine (ppm) | Voltage V | Free Residual Chlorine (ppm) | Voltage V | Free Residual Chlorine (ppm) | Voltage V | Free Residual Chlorine (ppm) |
| 507 | 15.9 | 80 | 22.6 | 115 | 28.6 | 138 | | |
| 1000 | 11.3 | 115 | 14.8 | 168 | 18.5 | 210 | | |
| 2060 | 7.9 | 165 | 10.1 | 218 | 12 | 275 | 13.8 | 335 |
| 3000 | 7.3 | 195 | 9 | 255 | 10.4 | 327 | | |
| 4000 | 6.6 | 225 | 8 | 300 | 9 | 383 | 10.4 | 452 |

(Embodiment 2)

Figure 4:
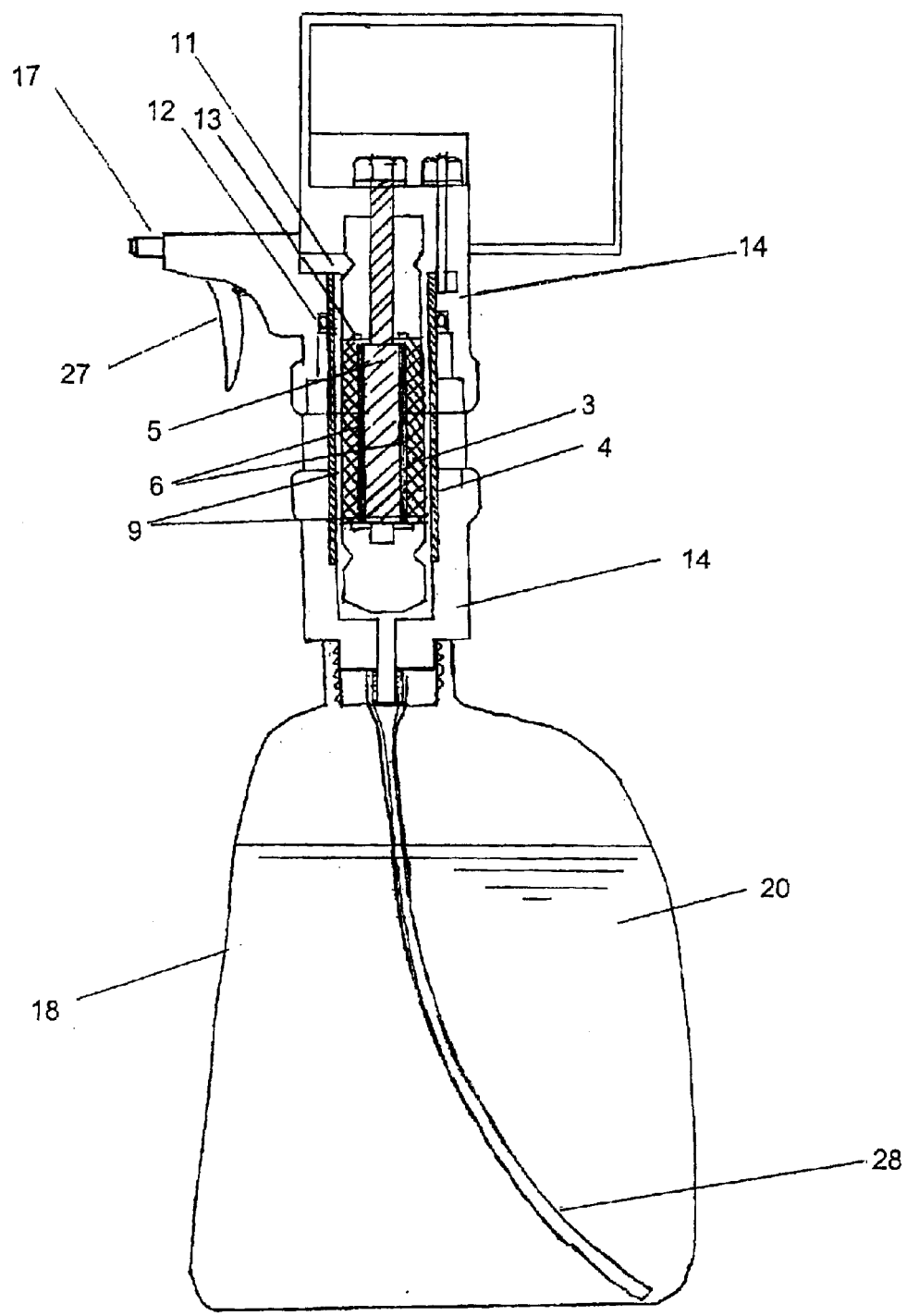
FIG. 4 is a cross-sectional view of an electrolytic spray container with a lever-type spray nozzle (17).

The present embodiment is a further compact, lighter and simpler example than Embodiment 1 in which an electrolyzer is contained in a regularly available push-button type spray container. The mode of the embodiment is described in accordance with FIG. 4.

The electrolyzer (1) is set in between the spray nozzle portion (17) of the push-button type spray container and the container (18). The solution containing halogen ions was passed through a suction pipe (28) and the inter-electrode reaction portion (9) of the electrolyzer (1) while being electrolyzed, and became sterilizing wash water containing active oxygen and a hypo-halogen acid and was sprayed from the spray nozzle (17).

The nickel-ferrite anode (3) used in the present embodiment was a tubular shape with an electrode surface of 0.3 dm2, a length of 47 mm, and a diameter of 20 mm. The cathode (4) was a titanium pipe and the inter-electrode distance was set to be 1.5 mm. In addition, it was adjusted so that the amount of the solution discharged from the sterilizing wash water exit hole (11) was 60 ml/mn.

The following (1) to (4) were used as the solution containing halogen ions filled into the pressurizable solution container (18).

Furthermore, the reduction of the Free Residual Chlorine density can be limited to a minimum even after being sprayed into the air.

In the present embodiment, saline and sodium bromide with a weight ratio of 6:4 as the halogen ions were used. A mol ratio of 6:4 which is the best ratio in Japanese Laid-Open Patent No. H11-226092, was selected. The results of the embodiment are shown in Table 2.

Since the anode has a 0.3 dm2 electrode surface, which is ⅓ of the 1 dm2 anode electrode surface in Embodiment 1, the Free Residual Chlorine concentration is slightly low. However, it is sufficient for the concentration required for the sanitization/sterilization.

TABLE 2

| | Current | | | |
|---|---|---|---|---|
| | 3A | | 4A | |
| | Electric Conductivity | | | |
| µS/cm | Voltage V | Free Residual Chlorine (ppm) | Voltage V | Free Residual Chlorine (ppm) |
| 1000 | 14.2 | 33 | 16.8 | 41 |
| 2060 | 9.7 | 42 | 11.3 | 54 |
| 3000 | 8.6 | 49 | 10.2 | 62 |

(Embodiment 3)

When purified sterilizing water that is atomized through spraying comes in contact with the atmosphere, the active oxygen and hypo-halogen acid are decomposed, and consequently, the concentration of the Free Residual Chlorine may be significantly reduced.

In Embodiment 3, purified sterilizing water created through electrolyzing in Embodiment 2 was sprayed and its Free Residual Chlorine concentration was measured and compared with the created electrolyzed water.

Table 3 shows the results "I" was a measurement of the sample, which came out from the nozzle of the sterilizing wash water exit hole (17) having an internal diameter of 2 mm, when it was electrolyzed with an electrolytic current of 3 A in Embodiment 2.

"II" was measured after collecting 2 ml of it into a glass container and being left for 20 minutes.

"III" was approximately a 6 ml sample, for which a spray nozzle (17) for hair spray was attached, and was sprayed under the same conditions while electrolyzing, and collected in a 500 ml beaker.

TABLE 3

| | Free Residual Chlorine (ppm) | | | | | |
|---|---|---|---|---|---|---|
| | Current | | | | | |
| | 3A | | | 4A | | |
| µS/cm | I | II | III | I | II | III |
| 1000 | 33 | 24 | 22 | 41 | 29 | 26 |
| 2060 | 42 | 29 | 25 | 54 | 38 | 33 |
| 3000 | 49 | 34 | 29 | 62 | 41 | 35 |

In the case "II", the decrease in the Free Residual Chlorine concentration was approximately 5% in 20 minutes after it was electrolyzed and put in a container. The decrease due to spraying was approximately 12% on the average. Therefore, it sufficiently fulfills the 20 ppm that shows a normal sterilization effect.

A solution of inorganic acid such as a hydrochloric acid or organic acid such as acetate is filled into the pressurizable solution container (18) in advance, and stored in a pressurized state by force 4 filing an inert gas or air, and the container is attached to the feed hole (19) to remove deposits such as hydroxide metals deposited on the cathode.

A solution of an inorganic acid such as a hydrochloric acid or an organic acid such as acetic acid is filled into a pressurizable solution container (18) in advance, and the pressurizable solution container (18) is attached to the feed hole (19) as required and then solution is fed to the electrolyzer (1) while the electrolysis is stopped, and then deposits such as hydroxide metals deposited on the cathode can be thoroughly dissolved and removed.

According to the present invention, a solution containing halogen ions is stored in a pressurizable solution container (18) which is a small container of 100 to 500 ml. This solution containing halogen ions is fed to the electrolyzer (1) and without using a pump, a very compact electrolyzed water generator can be created. As a result, it can conveniently have a high sanitization/sterilization effect as a portable sterilizing wash water hand spray anywhere and on anything.

The disclosure of Japanese Patent Application No. 2001-157680 filed on May 25, 2001 including specification, drawings and claims is incorporated herein by reference in its entirety.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

What is claimed is:

1. A method for generating sterilizing wash water, the method comprising:

storing a solution containing halogen ions in a pressurizable solution container, applying air pressure or inert gas pressure to the container, feeding the solution containing halogen ions to an electrolyzer, electrolyzing the solution, and discharging, by the air or inert gas pressure, electrolyzed solution as sterilizing wash water that is a product of the electrolysis from a sterilizing wash water exit hole.

2. The method for generating sterilizing wash water according to claim 1, wherein the electrolyzer is structured such that an anode comprising a ferrite pipe or rod, or a conductive metal pipe or rod that is thermal sprayed with a ferrite and a cathode comprising a conductive metal pipe are concentrically arranged with an inter-electrode distance of 1.1 to 9 mm, and in the electrolyzing the solution, the solution containing halogen ions flows and is electrolyzed between the the anode and the cathode.

3. The method for generating sterilizing wash water according to claim 1, wherein the electrolyzer is made by steps comprising filling a soft conductive low-melting point metal or mercury into a ferrite rod with a long hole, placing a conductive rod terminal body in the long hole to create a terminal, and overlaying concentrically a conductive anti-corrosive metal pipe thereon to create a cathode.

4. The method for generating sterilizing wash water according to claim 1, wherein, the pressurizable solution container is detachable from the electrolyzer.

5. The method for generating sterilizing wash water according to claim 1, wherein an air pump or inert gas feeding means can be attached to an inlet of the pressurizable solution container.

6. The method for generating sterilizing wash water according to claim 1 wherein, a chloride or bromide of potassium or sodium is used individually or mixed as the solution containing halogen ions, and its combination, ratio or concentration thereof is changed depending on a purpose of use of the sterilizing wash water.

7. A portable apparatus for generating sterilizing wash water comprising:

a solution container in which pressure is applied, an electrolyzer connected to a sterilizing wash water exit hole with a ferrite anode, a battery, and a power control apparatus comprising a direct power board, and a control board that controls the electrolysis time.

8. The portable apparatus for generating sterilizing wash water according to claim 7, wherein a spray nozzle is attached to the sterilizing wash water exit hole and electrolyzed sterilizing wash water is sprayed to a target with the pressure of the solution container.

9. The portable apparatus for generating sterilizing wash water according to claim 7, wherein a solution of inorganic acid such as a hydrochloric acid or organic acid such as acetate is filled in to the solution container, an inert gas or air is filled in the solution container, the solution container is attached to a feed hole of the electrolizer, so that deposits deposited on a cathode is removed.

10. A method for removing deposits on a cathode of electrolyzer, the method comprising: filling a solution of inorganic acid such as a hydrochloric acid or organic acid such as acetate into a pressurizable solution container, filling an inert gas or air in the solution container, attaching the solution container to a feed hole of the electrolizer, and removing deposits such as hydroxide metals deposited on the cathode.

* * * * *